(12) United States Patent
Tanimura et al.

(10) Patent No.: US 10,542,910 B2
(45) Date of Patent: Jan. 28, 2020

(54) WEARABLE MEASUREMENT DEVICE AND MEASUREMENT METHOD

(71) Applicant: Sharp Kabushiki Kaisha, Sakai, Osaka (JP)

(72) Inventors: Motoki Tanimura, Sakai (JP); Shinichi Tanaka, Sakai (JP); Shin Sugiyama, Sakai (JP); Kota Nakamura, Sakai (JP); Takeshi Ojio, Sakai (JP); Akifusa Nakazawa, Sakai (JP); Shigenori Kitani, Sakai (JP); Yuki Chiyoda, Sakai (JP); Kaori Okazaki, Sakai (JP); Saki Tanaka, Sakai (JP)

(73) Assignee: Sharp Kabushiki Kaisha, Sakai (JP)

( * ) Notice: Subject to any disclaimer, the term of this patent is extended or adjusted under 35 U.S.C. 154(b) by 156 days.

(21) Appl. No.: 15/307,542

(22) PCT Filed: Mar. 18, 2015

(86) PCT No.: PCT/JP2015/058135
§ 371 (c)(1),
(2) Date: Oct. 28, 2016

(87) PCT Pub. No.: WO2015/166740
PCT Pub. Date: Nov. 5, 2015

(65) Prior Publication Data
US 2017/0049361 A1 Feb. 23, 2017

(30) Foreign Application Priority Data

Apr. 30, 2014 (JP) ................. 2014-094065

(51) Int. Cl.
*A61B 5/11* (2006.01)
*A61B 5/00* (2006.01)
*A61B 5/22* (2006.01)

(52) U.S. Cl.
CPC .............. *A61B 5/11* (2013.01); *A61B 5/6815* (2013.01); *A61B 5/7235* (2013.01); *A61B 5/228* (2013.01);
(Continued)

(58) Field of Classification Search
CPC ......... A61B 5/11; A61B 5/228; A61B 5/4205; A61B 5/4542; A61B 5/6814; A61B 5/6815; A61B 5/682; A61B 5/7207; A61B 5/7235
See application file for complete search history.

(56) References Cited

U.S. PATENT DOCUMENTS 5,067,488 A * 11/1991 Fukada ................... A61B 5/11
600/590
6,893,406 B2 * 5/2005 Takeuchi ............. A61B 5/0088
600/590

(Continued)

FOREIGN PATENT DOCUMENTS

| JP | 11-123185 A | 5/1999 |
|---|---|---|
| JP | 2012-075758 A | 4/2012 |

*Primary Examiner* — Devin B Henson
(74) *Attorney, Agent, or Firm* — Keating & Bennett, LLP

(57) ABSTRACT

The wearable measurement device includes a mounting part for mounting the device to a human body, a variation detection part detecting a variation in distance from a predetermined portion of the human body, a posture detection part detecting a posture of the variation detection part in the case where the device is mounted to the human body through the mounting part, and a measurement part measuring the number of predetermined motions based on the variation detected by the variation detection part and the posture detected by the posture detection part. The variation detection part includes a light emitting unit and a light receiving unit, makes the light emitting unit emit light and the light receiving unit detect reflection light reflected at a predetermined portion, detects a distance from the predeter- (Continued)

mined portion and outputs an electric signal (voltage or current) in accordance with the detected distance at a predetermined sampling cycle.

5 Claims, 16 Drawing Sheets

(52) U.S. Cl.
CPC .......... *A61B 5/4205* (2013.01); *A61B 5/4542* (2013.01); *A61B 5/682* (2013.01); *A61B 5/6814* (2013.01); *A61B 5/7207* (2013.01); *A61B 2562/0219* (2013.01)

(56) References Cited

U.S. PATENT DOCUMENTS

| | | | | |
|---|---|---|---|---|
| 2006/0064037 A1* | 3/2006 | Shalon | ................. | A61B 5/0006 600/586 |
| 2009/0030346 A1* | 1/2009 | Kojima | ................... | A61B 5/11 600/590 |
| 2011/0276312 A1* | 11/2011 | Shalon | ..................... | A61B 5/11 702/187 |
| 2014/0251023 A1* | 9/2014 | Magomedov | ............ | A61B 5/11 73/779 |

* cited by examiner

F I G. 7

| ANGLE $\theta$ | WEIGHTING COEFFICIENT |
|---|---|
| 0 | 1 |
| $\theta 1$ | $\alpha 1$ |
| $\theta 2$ | $\alpha 2$ |
| ⋮ | ⋮ |

WEARABLE MEASUREMENT DEVICE AND MEASUREMENT METHOD

CROSS-REFERENCE TO RELATED APPLICATIONS

This application is the national phase under 35 U.S.C. § 371 of PCT International Application No. PCT/JP2015/058135 which has an International filing date of Mar. 18, 2015 and designated the United States of America.

FIELD

The present invention relates to a wearable measurement device measuring a predetermined motion while being mounted on a human body and to a measurement method therefor.

BACKGROUND

In recent years, prevention of lifestyle-related diseases, prevention of obesity, stress relief, beauty, brain activation and the like have gathered much attention, and thus equipment for management and improvement of health have been developed. For example, a chewing motion which is an action of digesting food has attracted attention as an action for bringing out change or vitality in the whole body through the brain.

For example, a device for detecting the number of chews is disclosed in which a microphone provided to an earphone-like or a headphone-like attachment member is placed near the mouth while the device is being worn, to detect sound generated by the movement of the jaw joint, sound generated by the contact of teeth and so forth from the sound detected by the microphone so as to detect the number of chews (see Japanese Patent Application Laid-Open Publication No. H11-123185).

SUMMARY

However, since the height, weight, age and the like are different for each user.

A predetermined motion such as the number of chews cannot be precisely measured by wearing the device disclosed in Japanese Patent Application Laid-Open Publication No. H11-123185 because the detected results for the number of chews include individual differences.

The present disclosure has been made in view of the circumstances described above, and aims to provide a wearable measurement device and a measurement method capable of precisely measuring a predetermined motion.

A wearable measurement device according to the present disclosure, including a mounting part for mounting the device to a human body, a variation detection part detecting a variation in distance from a predetermined portion of a human body, a posture detection part detecting a posture of the variation detection part in a case where the device is mounted to a human body through the mounting part, and a measurement part measuring the number of predetermined motions based on the variation detected by the variation detection part and the posture detected by the posture detection part.

The wearable measurement device according to the present disclosure, further including a decision part deciding a threshold in accordance with the posture detected by the posture detection part, wherein the measurement part is configured to count the number of predetermined motions if the variation detected by the variation detection part is larger than the threshold decided by the decision part.

The wearable measurement device according to the present disclosure, further including a human body motion detection part detecting a human body motion associated with the predetermined portion, wherein the measurement part is configured not to count the number of predetermined motions if the human body motion detection part detects a human body motion.

The wearable measurement device according to the present disclosure, further including a calculation part detecting variations multiple times by the variation detection part and calculating a statistical value of the detected multiple times of variations, wherein the measurement part is configured to count the number of predetermined motions if the variation detected by the variation detection part is larger than the statistical value calculated by the calculation part.

A measurement method according to the present disclosure is a measurement method by a wearable measurement device including a mounting part for mounting the device to a human body, and including the steps of detecting a variation in distance from a predetermined portion of a human body by a variation detection part, detecting a posture of the variation detection part in a case where the device is mounted to a human body through the mounting part, and measuring the number of predetermined motions based on the detected variation and posture.

According to the present disclosure, a predetermined motion may precisely be measured.

The above and further objects and features of the invention will more fully be apparent from the following detailed description with accompanying drawings.

BRIEF DESCRIPTION OF THE DRAWINGS

FIG. 7 is an explanatory view illustrating the relationship between a detected posture and a weighting coefficient.

DETAILED DESCRIPTION (Embodiment 1)

Figure 1:
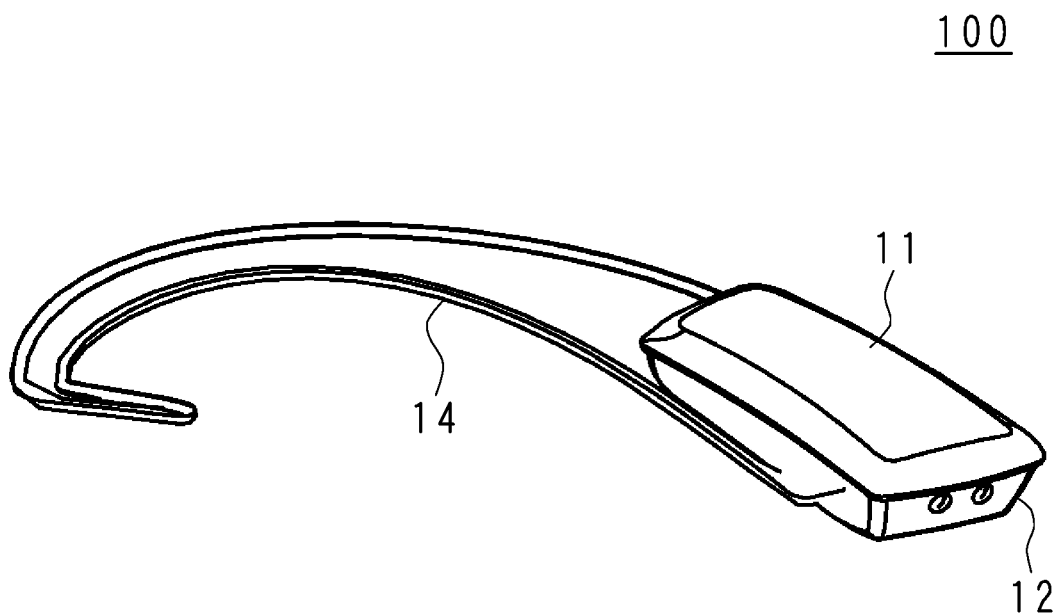
FIG. 1 is a perspective view illustrating the outer appearance of an example of a wearable measurement device according to an embodiment of the present invention.
Figure 2:
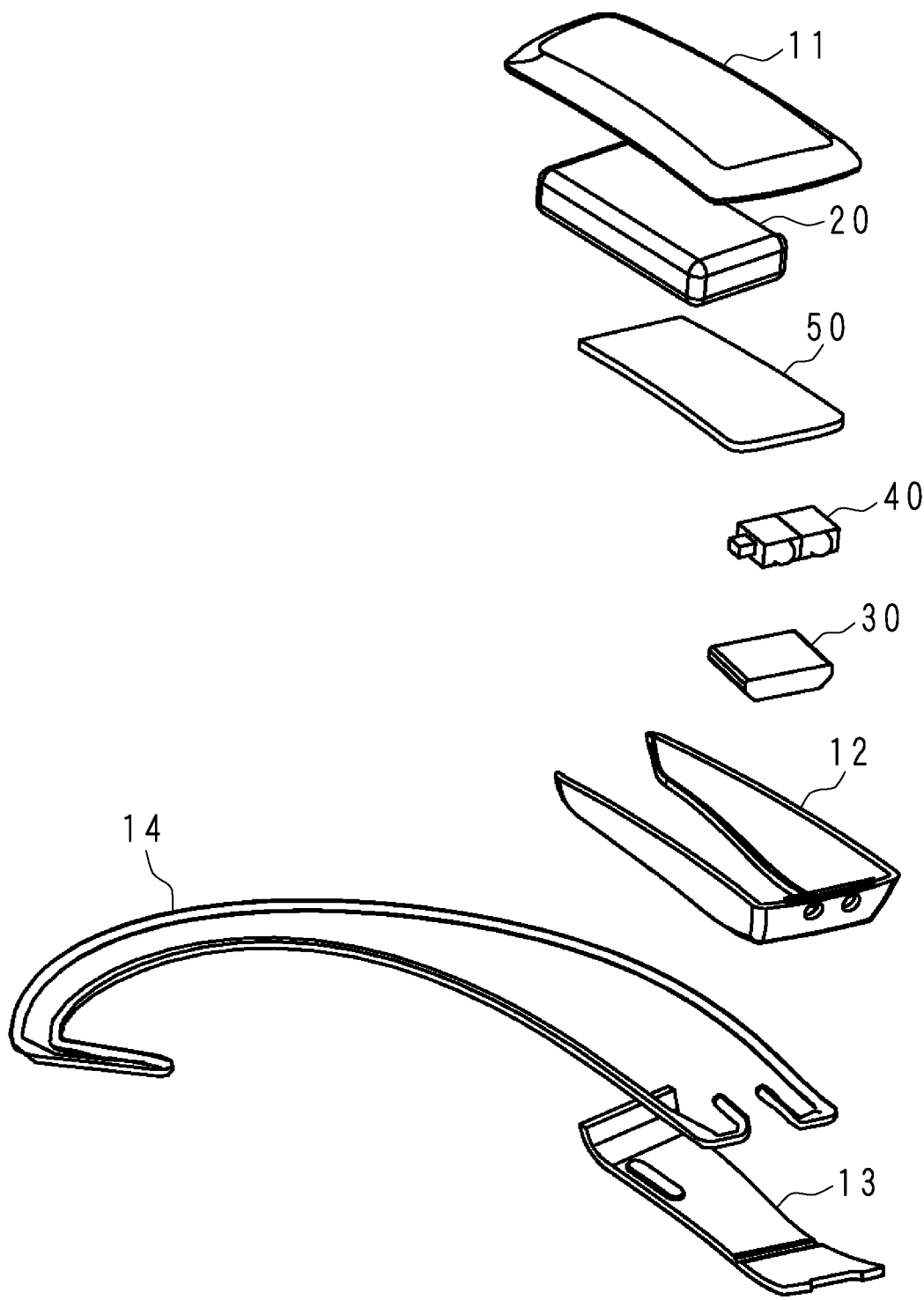
FIG. 2 is an exploded perspective view illustrating an example of the configuration of the wearable measurement device according to an embodiment of the present invention.
Figure 3:
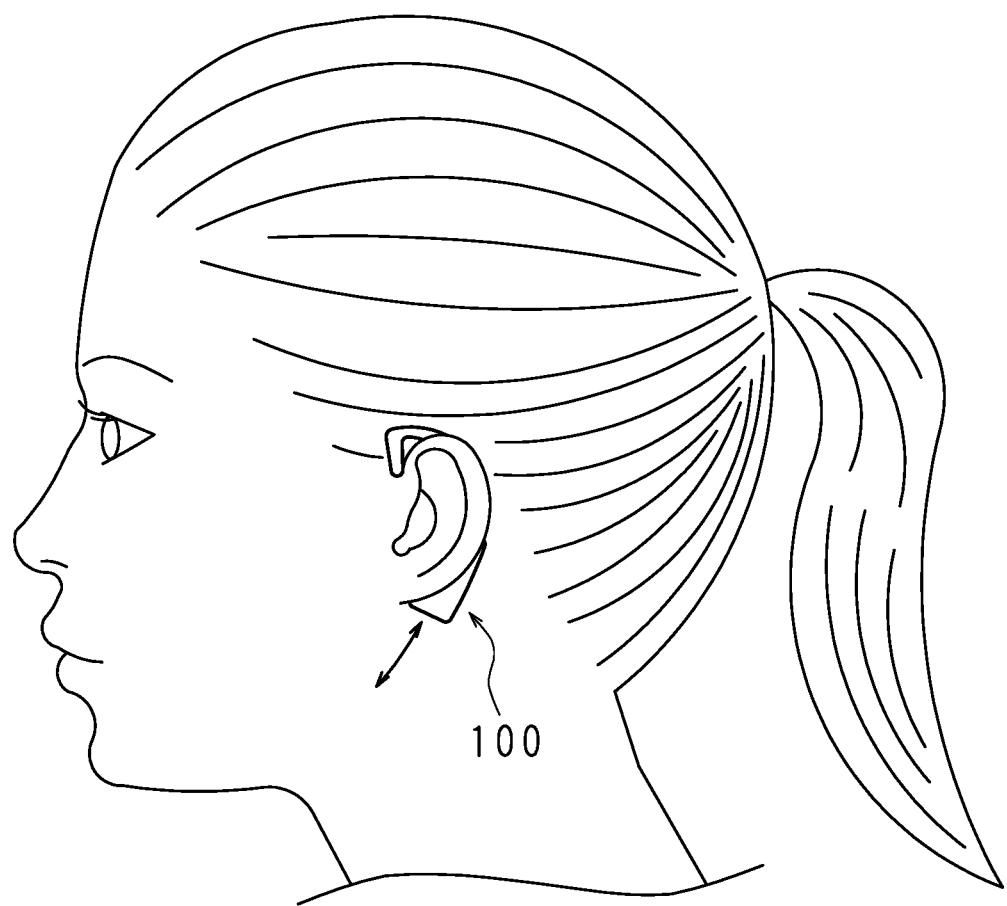
FIG. 3 is an explanatory view illustrating a mounting example to a human body of the wearable measurement device according to an embodiment of the present invention.

The present invention will be described below with reference to the drawings illustrating the embodiments thereof. FIG. 1 is a perspective view illustrating the outer appearance of an example of a wearable measurement device 100 according to the present embodiment. FIG. 2 is an exploded perspective view illustrating an example of the configuration of the wearable measurement device 100 according to the present embodiment. FIG. 3 is an explanatory view illustrating a mounting example to a human body of the wearable measurement device 100 according to the present embodiment. As illustrated in FIGS. 1 and 2, the wearable measurement device 100 comprises an upper case 11 and a lower case 12 that are fitted with each other to form a box, a clip 14 attached to one side of the lower case 12 and serving as a mounting part which is so curved as to be adapted to the shape of an ear, a back cover 13 sandwiching one end of the clip 14 between itself and the lower case 12, and also comprises a battery 20, a circuit board 50, a distance sensor 40 and a USB port 30 that are housed inside the upper case 11 and the lower case 12.

As illustrated in FIG. 3, the wearable measurement device 100 may be mounted to a human body by hanging the other end of the clip 14 over the upper part of an ear while placing the upper case 11 and lower case 12 that are fitted together behind the ear (earlobe). In the state where the wearable measurement device 100 is mounted to the ear, the distance sensor 40 is so arranged as to be able to detect the movement of a jaw as a predetermined portion and a variation in distance from the jaw.

The clip 14 serving as a mounting part may have an appropriate shape depending on a mounted portion of a human body. In the example illustrated in FIG. 3, the clip 14 having a shape adapted to the shape of the ear may be used as the mounting part. The structure of hanging over the ear allows the wearable measurement device 100 to be small and less noticeable during wearing.

The back cover 13 is made of, for example, material such as silicone to make the wearable measurement device 100 comfortable to wear when worn over the ear, while the back cover 13 is firmly in contact with the head behind the ear.

The battery 20 may supply required voltage to components such as the circuit board 50 and the distance sensor 40. Moreover, the battery 20 may be charged through the USB port 30.

Figure 4:
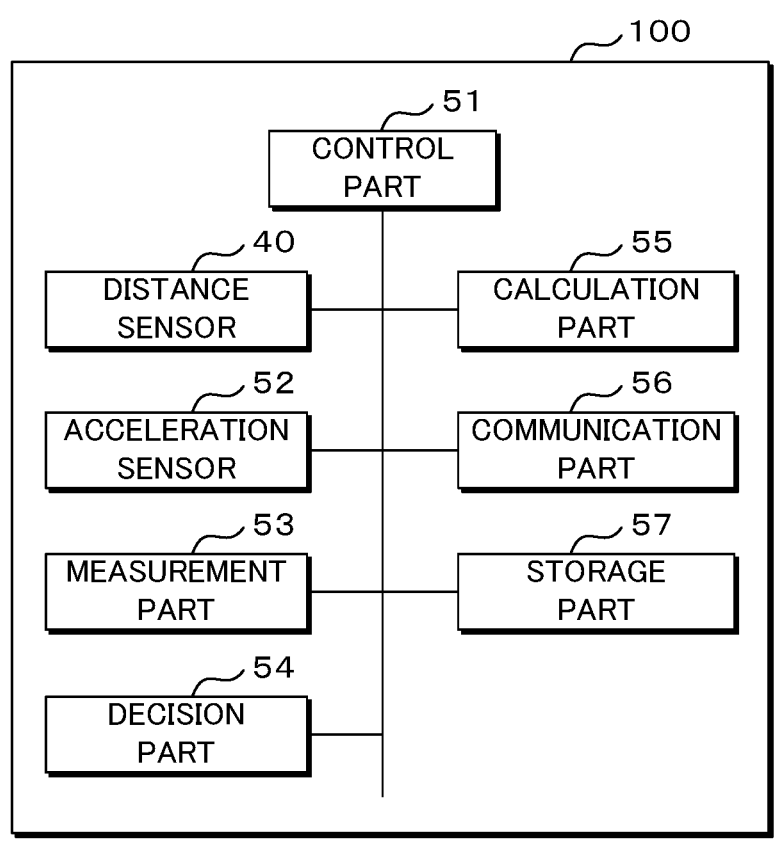
FIG. 4 is a block diagram illustrating an example of the configuration of the wearable measurement device according to an embodiment of the present invention.

FIG. 4 is a block diagram illustrating an example of the configuration of the wearable measurement device 100 according to the present embodiment. As illustrated in FIG. 4, the wearable measurement device 100 comprises, in addition to the distance sensor 40, a control part 51 controlling the entire device, an acceleration sensor 52, a measurement part 53, a decision part 54, a calculation part 55, a communication part 56, a storage part 57 and so forth. Each of these components is mounted to the circuit board 50.

The distance sensor 40 functions as a variation detection part. The distance sensor 40 detects the movement of a predetermined portion of a human body while not being in contact with the predetermined portion. Moreover, the distance sensor 40 detects a variation in distance from a predetermined portion of the human body. The predetermined portion may be, for example, a jaw (more specifically, lower jawbone).

The distance sensor 40 includes a light emitting unit such as an infrared light emitting diode and a light receiving unit such as a photo transistor, makes the light emitting unit emit light, detects reflection light reflected at a predetermined portion by the light receiving unit, and outputs an electric signal (voltage or current) in accordance with the intensity of the detected reflection light at a predetermined sampling cycle (0.2 seconds, for example). In the case where the predetermined portion is a jaw, the movement of the jaw changes the distance between the distance sensor 40 and the jaw. For example, voltage with a large peak value is output if the distance from the predetermined portion is short, whereas voltage with a small peak value is output if the distance from the predetermined portion is long. In the present embodiment, the movement of a predetermined portion to be detected by the distance sensor 40 or the variation in distance from the predetermined portion includes voltage output by the distance sensor 40.

The measurement part 53 includes an AD conversion part, and measures the number of chews as a predetermined motion based on the movement detected by the distance sensor 40. If chewing is performed once, the timing when the distance between the distance sensor 40 and the predetermined portion is minimum occurs once, which causes the voltage output by the distance sensor 40 to have a peak value once. By detecting the peak value of the variation obtained at a predetermined sampling cycle, the number of motions (number of chews) at the predetermined portion may be measured.

As described above, the distance sensor 40 is not in contact with the predetermined portion, which would not hinder a predetermined motion even if the predetermined portion moves along with the predetermined motion. Moreover, no sense of discomfort or no unpleasant feeling occurs while the wearable measurement apparatus 100 is worn, since the distance sensor 40 is not in contact with the predetermined portion. Furthermore, the distance sensor 40 is relatively inexpensive, has a simple structure, and does not require the use of an electromyograph, which can therefore measure the number of chews as a predetermined motion at low cost and with a simple structure of hanging the clip 14 over the ear.

Moreover, the measurement part 53 measures the number of chews as a predetermined motion. Thus, the number of chews may be measured with an inexpensive and simple structure without hindering the chewing.

In addition, the clip 14 may be made elastic so that the wearable measurement device 100 may be attached to clothes by pinching a collar or the like of the clothes between the clip 14 and the back cover 13 while not being used, which allows the user to easily carry the wearable measurement device 100 and to use it immediately when desired, thereby enhancing the convenience.

The acceleration sensor 52 functions as a human body motion detection part. The acceleration sensor 52 detects a human body motion associated with a predetermined portion. The human body motion associated with a predetermined portion (jaw, for example) may include speaking, nodding, sneezing, swallowing, head shaking and so forth. That is, the acceleration sensor 52 detects at least one of speaking, nodding, sneezing, swallowing and head shaking as a human body motion.

The acceleration sensor 52 may employ, for example, a piezoresistive three-axis acceleration sensor, a capacitive three-axis acceleration sensor or a piezoelectric three-axis acceleration sensor, and may measure acceleration speed in three directions of XYZ axes. It is noted that the acceleration sensor 52 may alternatively be two-axis acceleration sensor, not limited to the three-axis acceleration sensor.

The control part 51 has the function of a correction part, and corrects the measurement result from the measurement part 53 based on the human body motion detected by the acceleration sensor 52. For example, if a human body motion is detected by the acceleration sensor 52 in the case where chewing is measured once by the measurement part 53 and the number of chews is increased by one, the chewing measured by the measurement part 53 is regarded as being caused by a predetermined portion associated with the human body motion and, for example, the number of chews is not measured (correction is made to subtract one from the measured number of chews). This can prevent erroneous measurement due to a human body motion such as speaking, nodding, sneezing, swallowing or head shaking, and can therefore precisely measure a predetermined motion (number of chews, for example).

Moreover, the acceleration sensor 52 functions as a posture detection part. The acceleration sensor 52 detects the posture of the distance sensor 40 (or wearable measurement device 100 itself) in the case where the wearable measurement device 100 is mounted to a human body by the clip 14. That is, the acceleration of gravity on earth is measured by the acceleration sensor 52, to detect the posture (inclination) of the distance sensor 40. For example, the relationship between a reference posture (reference direction) of the distance sensor 40 when mounted and the gravity direction may be determined in advance, and an individual difference at the time of mounting depending on the height, weight, age and the like of the user may be specified in accordance with the difference (difference in angles) between the gravity direction and the reference direction.

The decision part 54 determines a threshold in counting of the number of chews as a predetermined motion in accordance with the posture detected by the acceleration sensor 52. The threshold is decided so that the individual difference of the user may be taken into consideration.

The calculation part 55 detects variations by the distance sensor 40 multiple times, and calculates a statistical value of the detected multiple times of variations. The statistical value may be an intermediate value (median value) between the maximum value and the minimum value of the detected multiple times of variations, or a mean value of the detected multiple times of variations.

The communication part 56 communicates with external equipment (display device) provided with a display screen, such as a smartphone, a mobile phone, a tablet, a personal computer or the like provided externally.

The storage part 57 stores predetermined information. The predetermined information will be described later.

Figure 5:
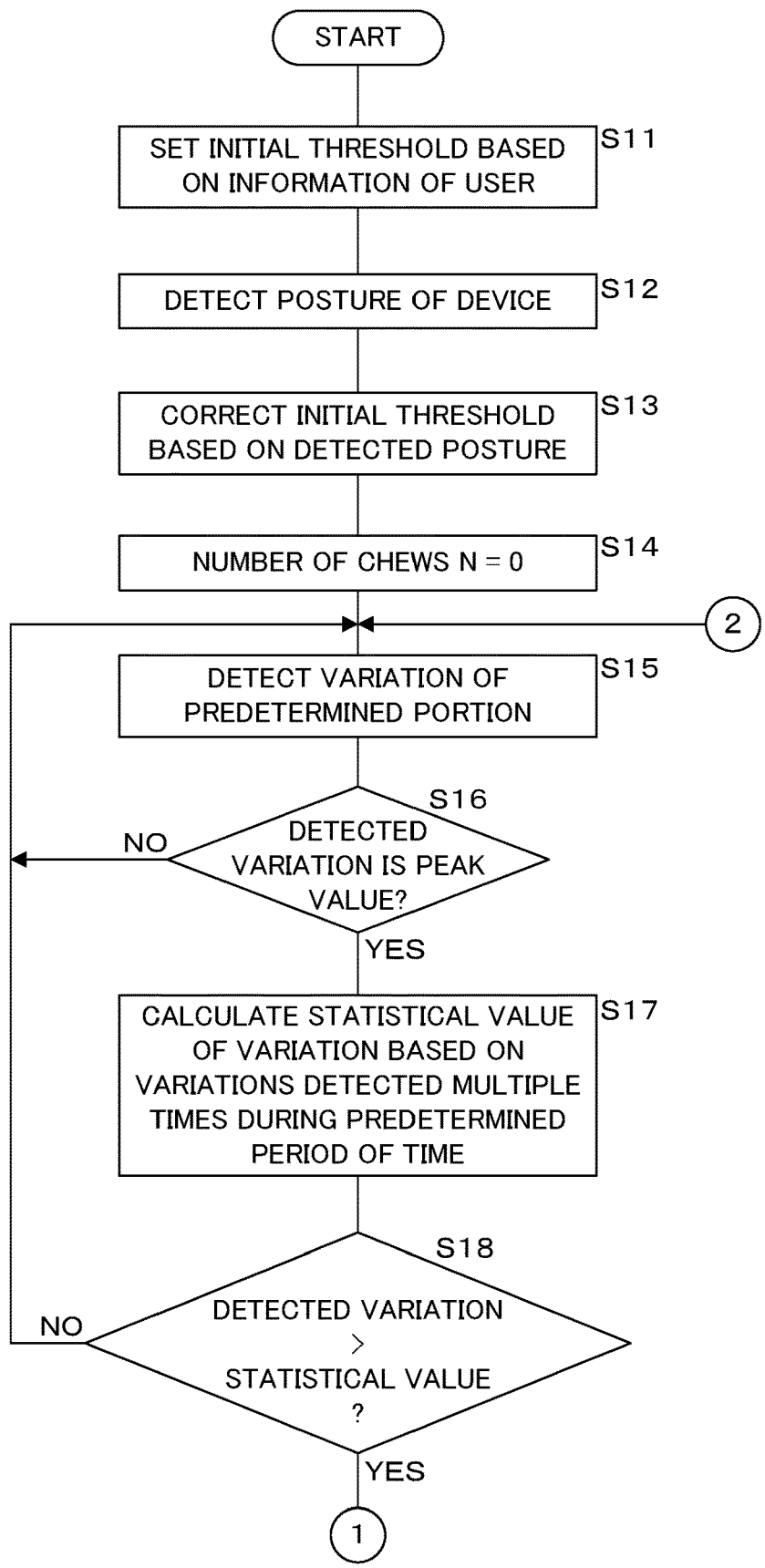
FIG. 5 is a flowchart illustrating an example of the processing procedure for measuring the number of chews measured by the wearable measurement device according to an embodiment of the present invention.
Figure 6:
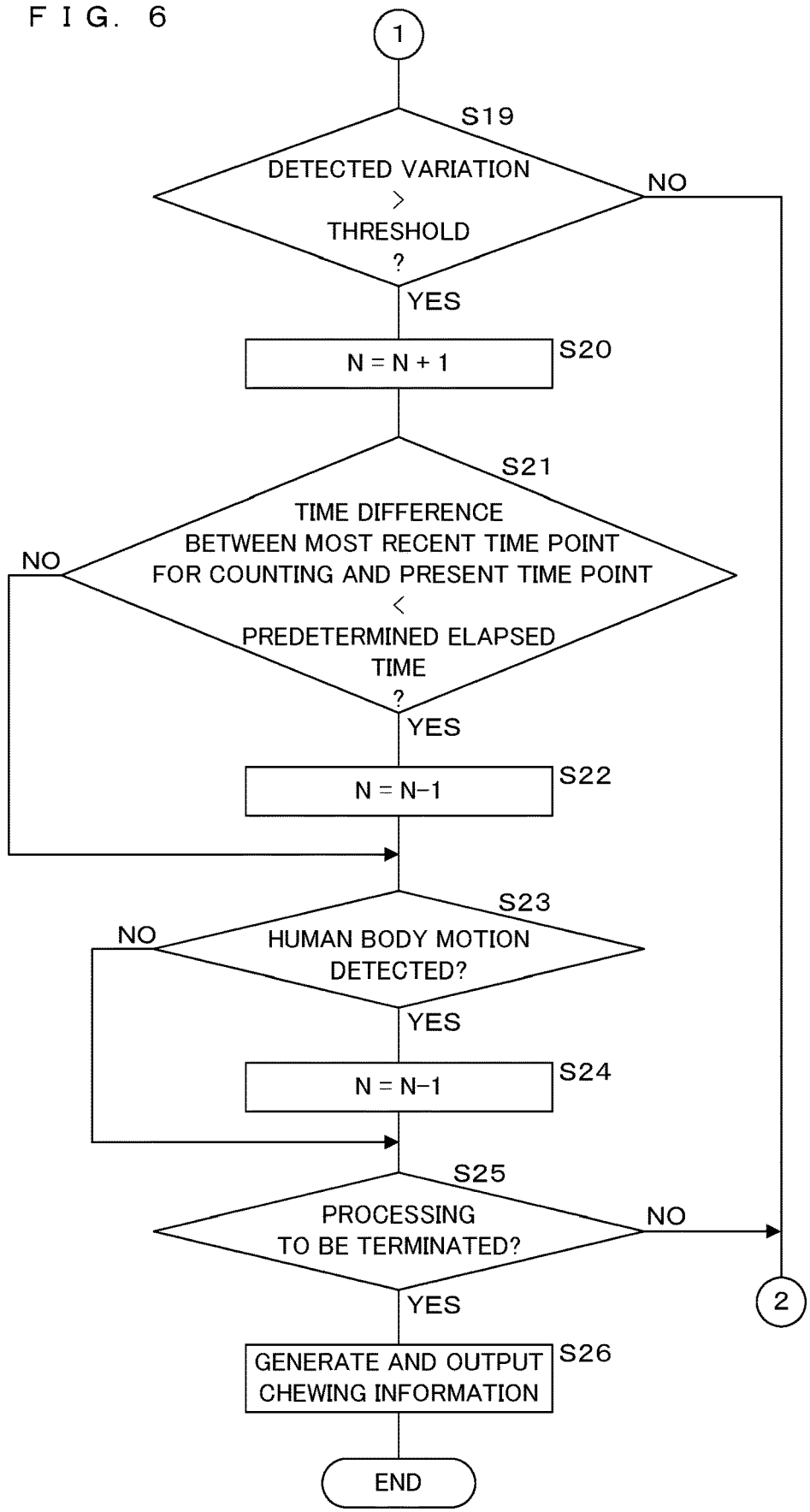
FIG. 6 is a flowchart illustrating an example of the processing procedure for measuring the number of chews measured by the wearable measurement device according to an embodiment of the present invention.

Next, measurement for the number of chews by the wearable measurement device 100 according to the present embodiment will be described in detail. FIGS. 5 and 6 show a flowchart illustrating an example of the processing procedure for measuring the number of chews by the wearable measurement device 100 according to the present embodiment. For the sake of simplicity, the control part 51 is described below as the processing subject.

The control part 51 sets an initial threshold C0 based on the information of the user (S11). The initial threshold C0 is an initial value of the threshold, which is used in measurement of the number of chews for determining whether or not chewing is performed. The information of the user may include, for example, gender, age, height, weight and so forth. The information of the user may be input from external equipment (e.g., smartphone, tablet or the like) through the communication part 56. The input information (personal information) is categorized by user and stored in the storage part 57.

The control part 51 controls the acceleration sensor 52 to detect the posture of the wearable measurement device 100 (distance sensor 40) at the time when the wearable measurement device 100 is mounted over the ear (S12). For example, the relationship between a reference posture (reference direction) of the distance sensor 40 when mounted and the gravity direction may be determined in advance, and the difference (difference in angles) between the gravity direction and the reference direction may be detected.

The control part 51 controls the decision part 54 to correct the initial threshold C0 which is set using a weighting coefficient based on the detected posture, to decide a threshold C (S13).

FIG. 7 is an explanatory view illustrating the relationship between the detected posture and the weighting coefficient. As described earlier, the posture of the distance sensor 40 may be represented by an angle formed by the reference posture (reference direction) of the distance sensor 40 and the gravity direction. The angle formed by the gravity direction and the reference direction representing the reference posture of the wearable measurement device 100 when worn over the ear is set to 0. As illustrated in FIG. 7, if the angle is 0, the weighting coefficient may be set to 1. Here, the initial threshold C0 may be used as the decided threshold C without any correction.

Furthermore, assume that the reference direction is displaced from the gravity direction at the time when the wearable measurement device 100 is mounted due to the individual difference of the user, resulting in the angle of $\theta 1$. Here, if the weighting coefficient is assumed as $\alpha 1$, the threshold C may be obtained by $\alpha 1 \times$the initial threshold C0. Same applies to the other angles (postures). By changing the threshold C based on the posture detected by the acceleration sensor 52, the individual difference of the user may be assimilated and the number of chews may precisely be measured.

For example, if the distance between the distance sensor 40 and the predetermined portion is long while the peak value in the variations detected by the distance sensor 40 is small when the wearable measurement device 100 is mounted to a human body with the clip 14, the threshold C is made smaller. If, on the other hand, the distance between the distance sensor 40 and the predetermined portion is short while the peak value in variations detected by the distance sensor 40 is large when the wearable measurement device 100 is mounted to a human body with the clip 14, the threshold C is made larger. Accordingly, the individual difference of the user in the mounted state may be assimilated and thus the number of predetermined motions (chews) may precisely be measured.

The control part 51 sets the number of chews N to 0 (S14), and controls the distance sensor 40 to detect variation in a predetermined portion (jaw, lower jawbone) (S15). In the description below, voltage (movement of a predetermined portion or variation in distance from a predetermined portion) output by the distance sensor 40 at a predetermined sampling cycle (0.2 seconds, for example) is represented in time series by A1, A2, A3, . . . , A(i−1), Ai, A(i+1), . . . (i is an integer).

The control part 51 determines whether or not the detected variation is a peak value (S16). The condition for determining whether or not the variation is a peak value is as follows: the variation Ai may be determined as being the peak value if both of the expressions (1) and (2) are satisfied, whereas the variation Ai may be determined as not being the peak value if either one of the expressions is not satisfied.

$$Ai > A(i-1) \tag{1}$$

$$Ai > A(i+1) \tag{2}$$

$$A\max = \operatorname{Max}(A(i-5), \ldots A(i+5)) \tag{3}$$

$$A\min = \operatorname{Min}(A(i-5), \ldots A(i+5)) \tag{4}$$

$$A\operatorname{dif} = (A\max - A\min) \times 0.5 + A\min \tag{5}$$

$$Ai > A\operatorname{dif} \tag{6}$$

If the detected variation is not the peak value (NO at S16), the control part 51 continues the processing at and after step S15. If the detected variation is the peak value (YES at S16), the control part 51 controls the calculation part 55 to calculate the statistical value of variation based on the variations detected multiple times during a predetermined period of time (S17), and determines whether or not the detected variation is larger than the calculated statistical value (S18).

The detected variation is assumed as Ai. The predetermined period of time may be, in the case where the variation Ai corresponds to a reference time point for example, a period from five sampling cycles before the reference time point to five sampling cycles after the reference time point. That is, the statistical value is calculated using variations for ten times from A(i−5) to A(i+5) except for Ai. A maximum value Amax in the variations may be calculated from the expression (3), a minimum value Amin may be calculated from the expression (4), and a statistical value Adif may be calculated from the expression (5). That is, the statistical value may be an intermediate value (median value) between the maximum value and the minimum value of variations detected multiple times. It is noted that a mean value of variations detected multiple times may also be employed in place of the median value. Furthermore, the multiple times are not limited to five times before and five times after the reference time point, but may be other number of times, and the number of times may be different before and after the reference time point.

Whether the detected variation is larger than the calculated statistical value may be determined from the expression (6).

If the detected variation is not larger than the statistical value (NO at S18), the control part 51 determines that the detected variation is caused by noise, and continues the processing at and after step S15 without immediately counting the number of chews.

If the detected variation is larger than the statistical value (YES at S18), the control part 51 determines that the detected variation is not caused by noise, and performs the processing of the subsequent step S19 so as to measure the number of chews.

Figure 8A:
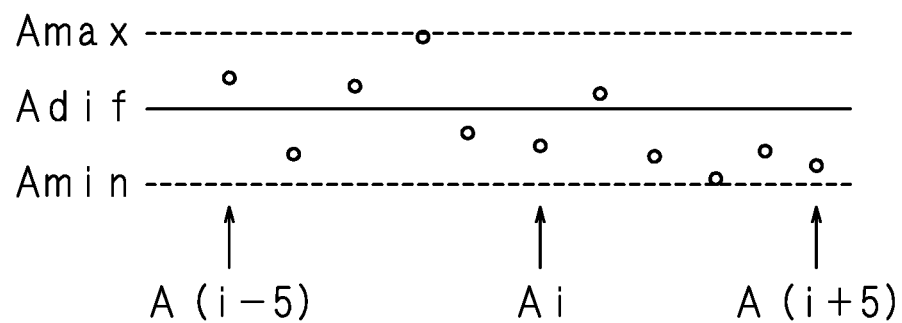
FIG. 8A is a schematic view illustrating the relationship between a detected variation and a statistical value.
Figure 8B:
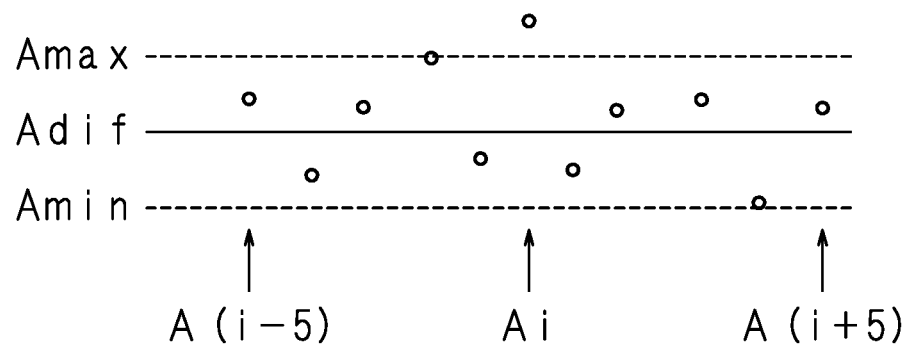
FIG. 8B is a schematic view illustrating the relationship between a detected variation and a statistical value.

FIGS. 8A and 8B are schematic views illustrating the relationship between a detected variation and a statistical value. In FIGS. 8A and 8B, the detected variation is assumed as Ai. The maximum value Amax is the maximum value among variations corresponding to ten times from A(i−5) to A(i+5) except for Ai. Moreover, the minimum value Amin is the minimum value among variations corresponding to ten times from A(i−5) to A(i+5) except for Ai. The statistical value Adif is an intermediate value (median value) between the maximum value Amax and the minimum value Amin.

As illustrated in FIG. 8A, if the detected variation Ai is equal to or smaller than the statistical value Adif, the variation Ai is regarded as being caused by noise or the like, and thus is not considered in counting the number of chews. If, on the other hand, the detected variation Ai is larger than the statistical value Adif as illustrated in FIG. 8B, the variation Ai is regarded as being caused by chewing, not noise, and is thus considered in counting. Such comparison between the detected variation and the statistical value ensures detection of the peak value of the variations obtained at a predetermined sampling cycle, and prevents erroneous measurement of the number of predetermined motions based on a variation with a small peak due to noise or the like.

The control part 51 determines whether or not the detected variation is larger than the decided threshold C (S19).

$$A\max = \operatorname{Max}(A(i-5), \ldots A(i)) \tag{7}$$

$$A\min = \operatorname{Min}(A(i-5), \ldots A(i)) \tag{8}$$

$$Aid = A\max - A\min \tag{9}$$

$$Aid > C \tag{10}$$

At step S19, the detected variation Aid is different from the variation at step S18, and may be calculated from the expressions (7), (8) and (9). Moreover, whether the detected variation Aid is larger than the decided threshold C may be determined from the expression (10). That is, if the maximum value of the variation Ai at the reference time point and the variations detected five times before the reference time point is assumed as Amax which is represented by the expression (7) while the minimum value of the variation Ai at the reference time point and the variations detected five times before the reference time point is assumed as Amin which is represented by the expression (8), the variation Aid is a difference between the maximum value Amax and the minimum value Amin as represented by the expression (9). It is noted that the number of variations detected before the reference time point may be any other number, not limited to five. Moreover, a variation detected after the reference time point may also be taken into consideration.

If the detected variation Aid is not larger than the threshold C (NO at S19), the control part 51 continues the processing at and after step S15. If the detected variation Aid is larger than the threshold C (YES at S19), the control part 51 assumes a value obtained by adding 1 to the number of chews N as the new number of chews N (S20). That is, the control part 51 increases the number of chews by 1.

In other words, the measurement part 53 counts the number of chews if the variation Aid detected by the distance sensor 40 is larger than the threshold C decided by the decision part 54.

As the threshold C is determined by quantifying in advance the variation detected by the distance sensor 40 in the case where a predetermined motion (e.g., chewing) is performed and the variation detected by the distance sensor 40 in the case where a human body motion (e.g., speaking)

is performed, determination can be made that the predetermined motion such as chewing is performed if the variation Aid detected by the distance sensor 40 is larger than the threshold C and that the human body motion such as speaking is performed if the variation Aid is not larger than the threshold C. Accordingly, the predetermined motion (chewing) may be distinguished from the human body motion such as speaking in the measurement of the predetermined motion, which allows for precise measurement of the number of predetermined motions.

The control part 51 determines whether or not the time difference between the most recent time point for counting (time point for counting the number of chews) and the present time point for counting is less than a predetermined elapsed time (e.g., 0.3 seconds) (S21). If the time difference is less than the predetermined elapsed time (YES at S21), the control part 51 determines that it is affected by noise because no one chews two times in 0.3 seconds during meal, and sets the value obtained by subtracting 1 from the number of chews N as the new number of chews N (S22). That is, the control part 51 reduces the number of chews N by 1. It is noted that the predetermined elapsed time is not limited to 0.3 seconds.

If the time difference is not less than the predetermined elapsed time (NO at S21), the control part 51 determines that it is not affected by noise and performs the processing of the subsequent step S23 without the processing of step S22. By the processing of step S21, whether or not the time difference between adjacent measurement time points for the number of chews is less than the predetermined elapsed time may be determined, to remove noise.

The control part 51 determines whether or not a human body motion is detected (S23), and if the human body motion is detected (YES at S23), a value obtained by subtracting 1 from the number of chews N is set to the new number of chews N (S24). If the number of chews N is not increased by 1 in the case where the human body motion is detected, it is not necessary to subtract 1 from the number of chews N.

That is, the acceleration sensor 52 detects a human body motion associated with a predetermined portion. The human body motion associated with a predetermined portion (jaw, for example) may include speaking, nodding, sneezing, swallowing, head shaking and so forth. If the human body motion is detected by the acceleration sensor 52, the measurement part 53 does not count the number of chews. For example, if a human body motion is detected by the acceleration sensor 52 in the case where chewing is measured once by the measurement part 53 and the number of chews is increased by one, the chewing measured by the measurement part 53 is regarded as being caused by a predetermined portion associated with the human body motion and, for example, the number of chews is not measured (correction is made to subtract one from the measured number of chews). This can prevent erroneous measurement due to human body motions such as speaking, nodding, sneezing, swallowing and head shaking, and can therefore precisely measure a predetermined motion.

If no human body motion is detected (NO at S23), the control part 51 performs the processing at step S25, which will be described later, without performing the processing of step S24.

The control part 51 determines whether or not the processing is terminated (S25), and if the processing is not terminated (NO at S25), continues the processing at and after step S15. If the processing is terminated (YES at S25), the control part 51 generates chewing information, outputs the generated chewing information through the communication part 56 to external equipment (smartphone, mobile phone, tablet, personal computer or the like) (S26), and terminates the processing. The details of the chewing information will be described later.

While the embodiment described above illustrated a configuration in which the variation detected by the distance sensor 40 in the case where chewing is performed and the variation detected by the distance sensor 40 in the case where speaking is performed are quantified in advance to determine the threshold C, the variation detected by the distance sensor 40 in the case where a human body motion other than speaking, for example, nodding, sneezing, swallowing, head shaking or the like is performed may also be quantified in advance to decide the threshold C. This allows for precise measurement of the number of chews by distinguishing a chewing motion from other human body motions such as nodding, sneezing, swallowing, head shaking and so forth.

Figure 9:
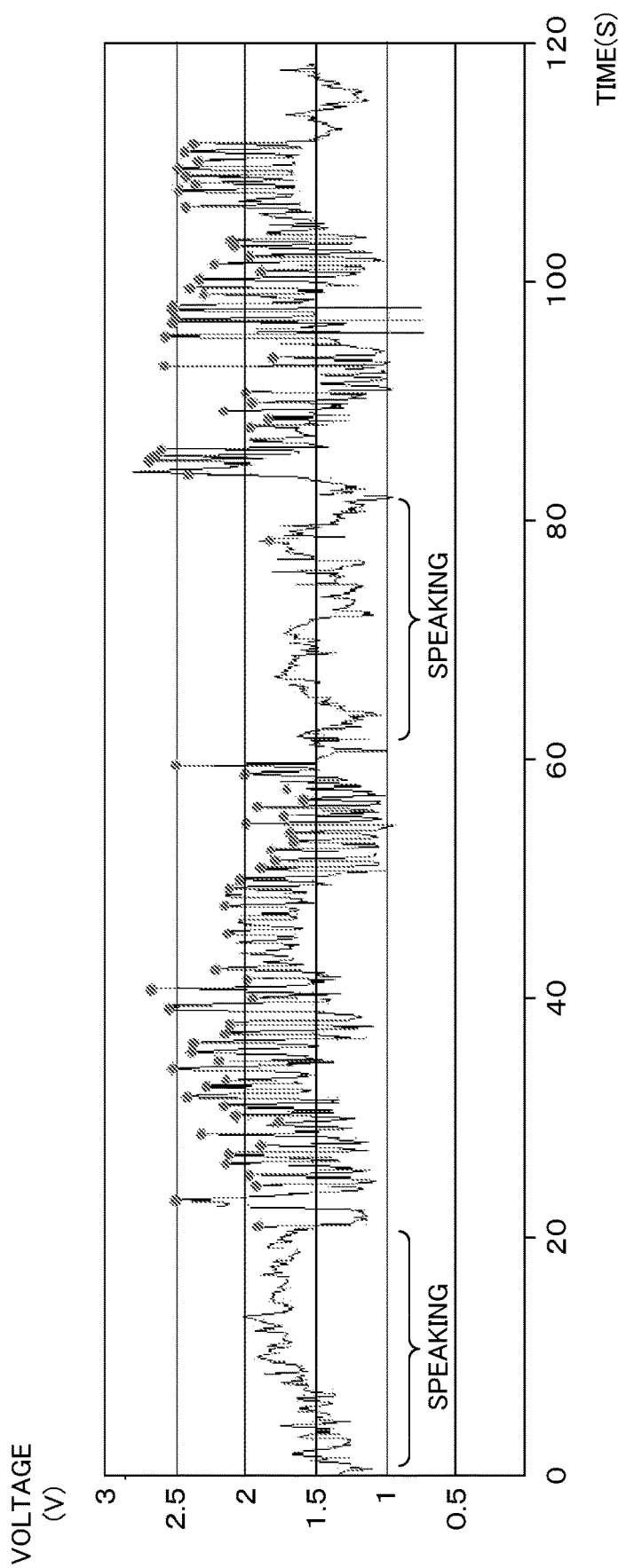
FIG. 9 is a time chart illustrating an example of the result of a mixture experiment for chewing and speaking measured by the wearable measurement device according to an embodiment of the present invention.

FIG. 9 is a time chart illustrating an example of the result of mixture experiment of chewing and speaking measured by the wearable measurement device 100 according to the present embodiment. In FIG. 9, the horizontal axis indicates time (seconds), whereas the vertical axis indicates voltage (variation) output by the distance sensor 40. FIG. 9 shows the result of an experiment where a tester eats a sandwich and chews for two minutes during which the tester speaks for 40 seconds. By performing the processing illustrated in FIGS. 5 and 6, the measurement result by the wearable measurement device 100 showed 74 times, while the actual times of chewing were 73 times. As such, even if a human body motion such as speaking is carried out, the number of chews may be precisely measured.

Next, a display mode for chewing information including the measured number of chews will be described. The control part 51 has a function of a generation part which generates chewing information including the number of chews and outputs the generated chewing information to external equipment through the communication part 56. It is noted that the generated chewing information may be stored in the storage part 57.

Figure 10:
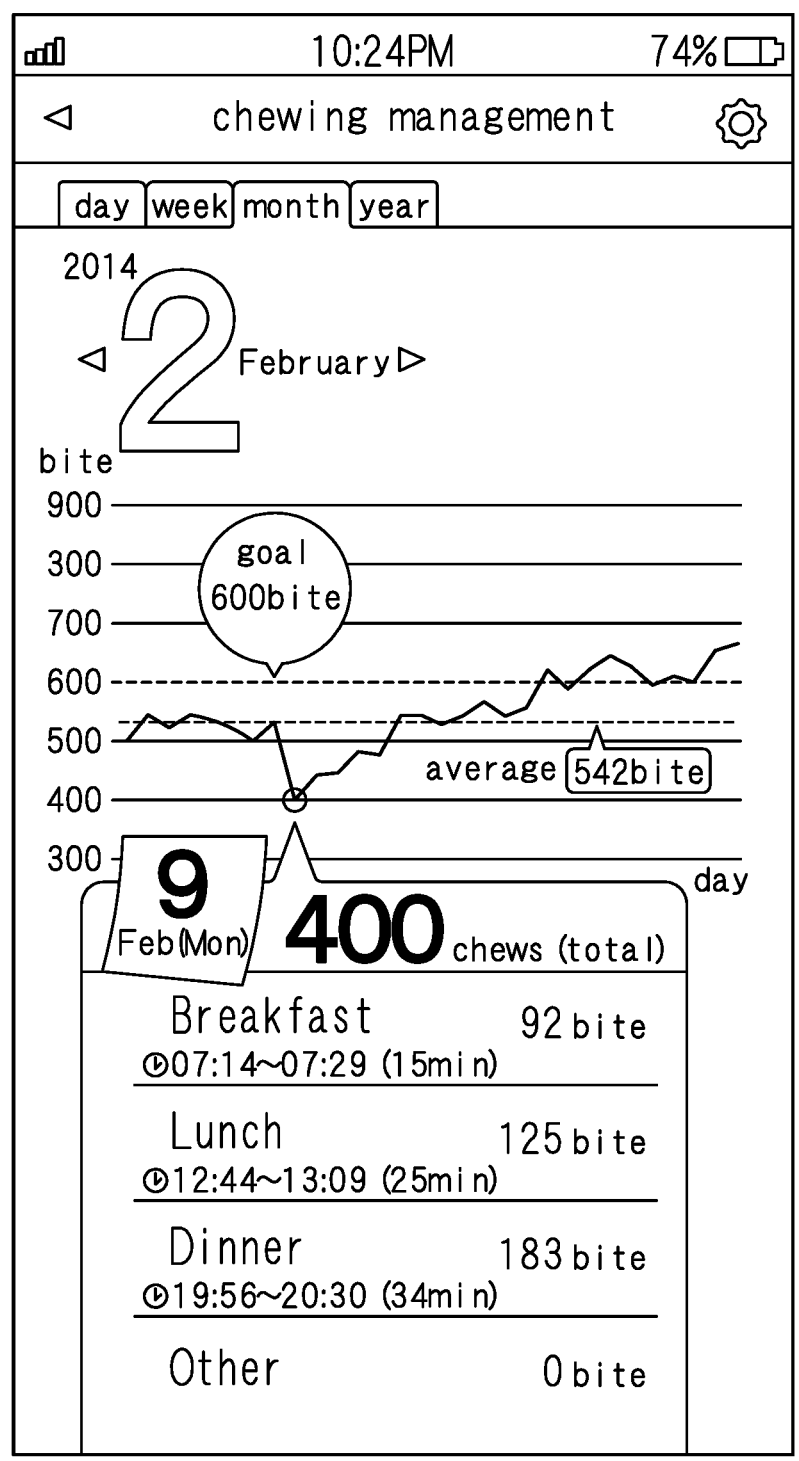
FIG. 10 is an explanatory view illustrating the first example of a display mode for chewing information.

FIG. 10 is an explanatory view illustrating the first example of a display mode for chewing information. As illustrated in FIG. 10, the chewing information includes the number of chews for each of breakfast, lunch and dinner per year, month, week and day, which may be visualized as a graph. This allows such information to be utilized as a general diary for diet.

Figure 11:
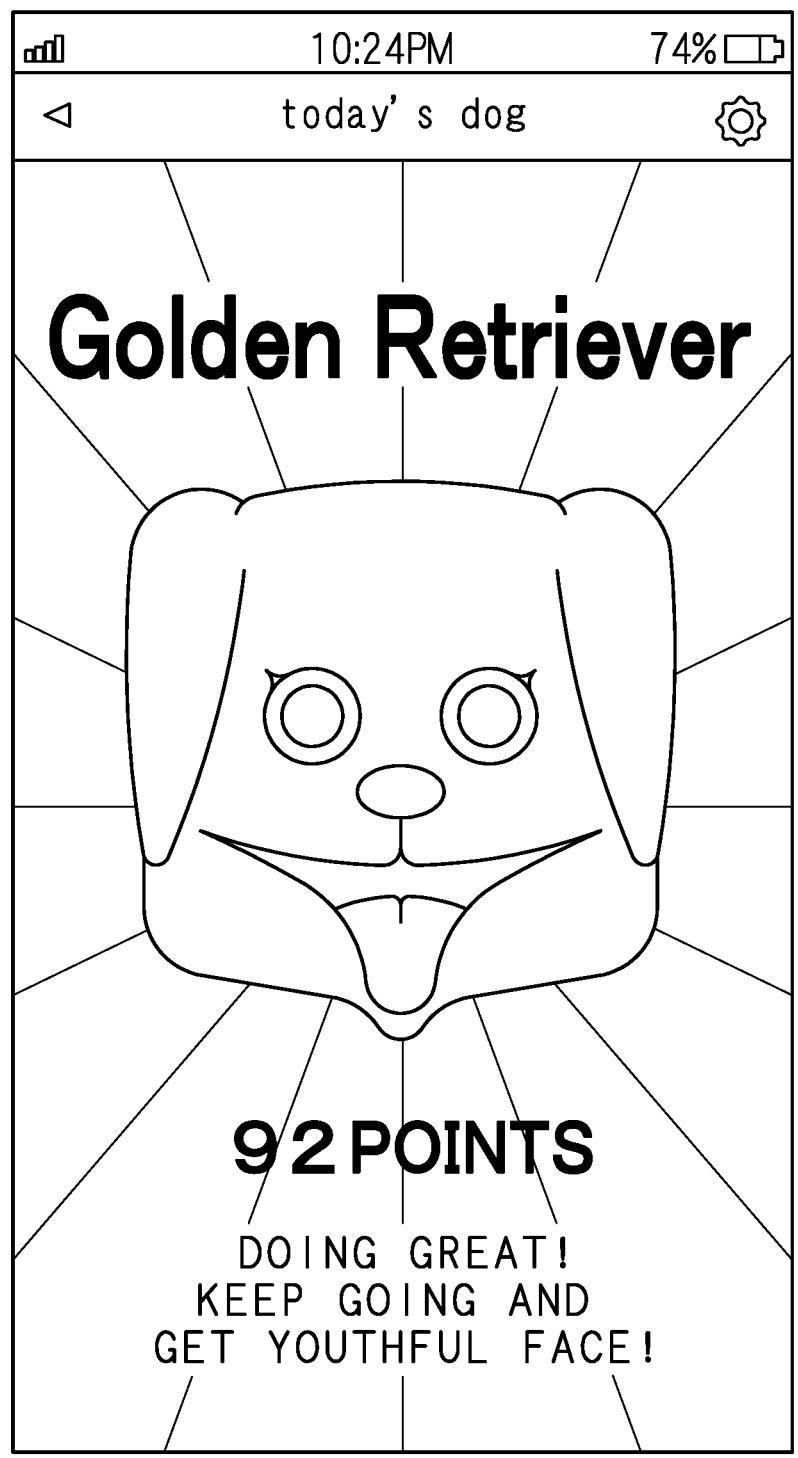
FIG. 11 is an explanatory view illustrating the second example of a display mode for chewing information.
Figure 12:
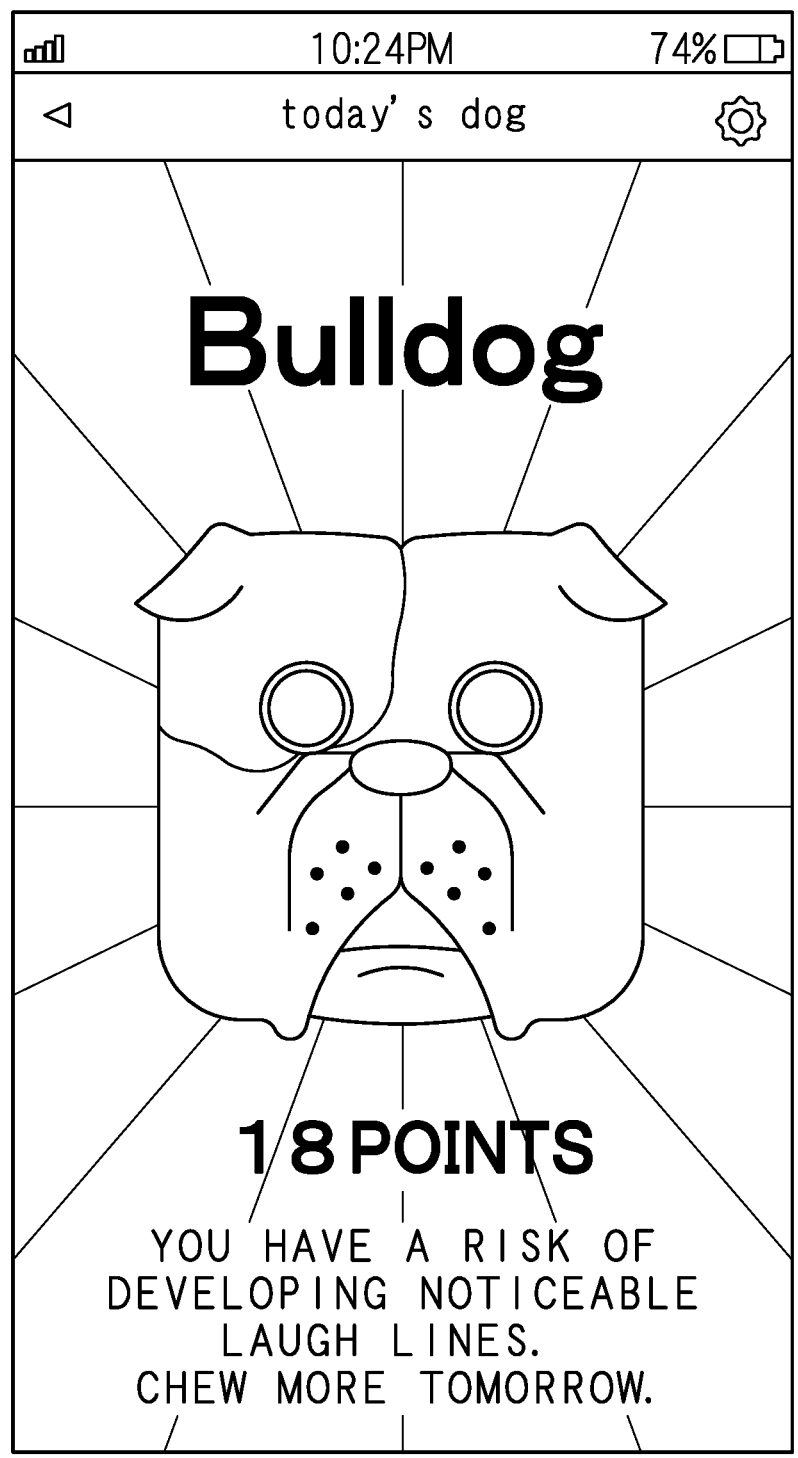
FIG. 12 is an explanatory view illustrating the second example of a display mode for chewing information.

FIGS. 11 and 12 are explanatory views illustrating the second example of display modes for chewing information. As illustrated in FIGS. 11 and 12, the chewing information includes the degree of achievement with respect to a target value for the number of chews. For example, as illustrated in FIG. 11, when the degree of achievement is reported daily to the user, if an obtained score exceeds a target value (the achievement is represented by a score in the example of FIG. 11), a character of a golden retriever which gives an impression of a fine-featured small face is displayed while a message indicating, for example, "Doing great! Keep going and get a youthful face!" is displayed in order to show the achievement. Moreover, as illustrated in FIG. 12, if the degree of achievement which is reported daily is lower than the target value (the achievement is represented by a score in the example of FIG. 12), a character of a bulldog which gives an impression of sagging cheek muscles is displayed while a message indicating, for example, "You have a risk of developing noticeable laugh lines. Chew more tomorrow" is displayed in order for the user to improve the achievement. As such, the degree of achievement for a target may be reported every day to urge the user to chew.

Figure 13:
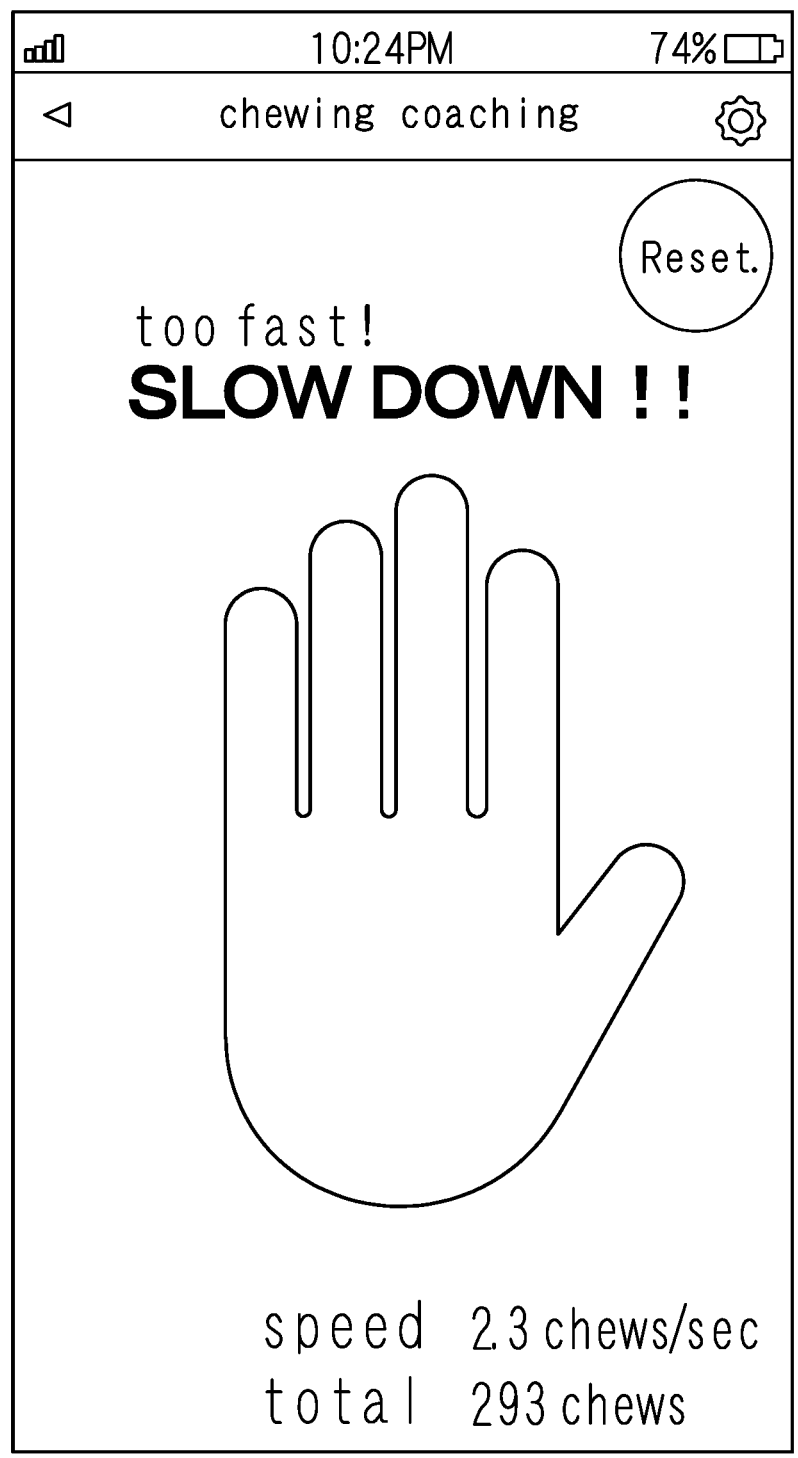
FIG. 13 is an explanatory view illustrating the third example of a display mode for chewing information.

FIG. 13 is an explanatory view illustrating the third example of a display mode for chewing information. As illustrated in FIG. 13, the chewing information includes the number of chews and the chewing speed. As illustrated in FIG. 13, if the chewing speed is too fast, a message instructing the user to slow down the chewing speed is immediately displayed by text, chart or the like. Accordingly, coaching in real time may be possible that shows an ideal way of eating (chewing speed).

Figure 14:
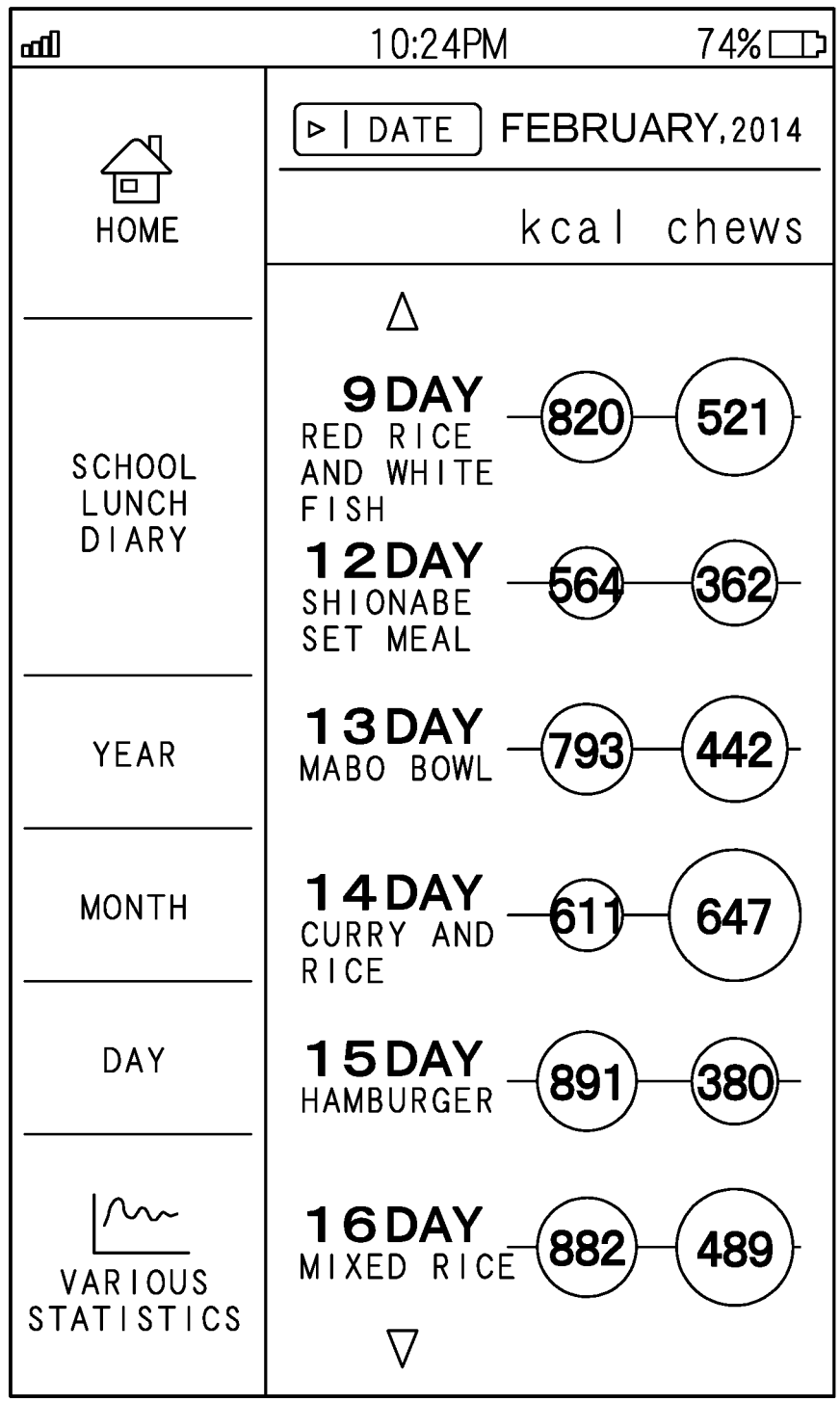
FIG. 14 is an explanatory view illustrating the fourth example of a display mode for chewing information.
Figure 15:
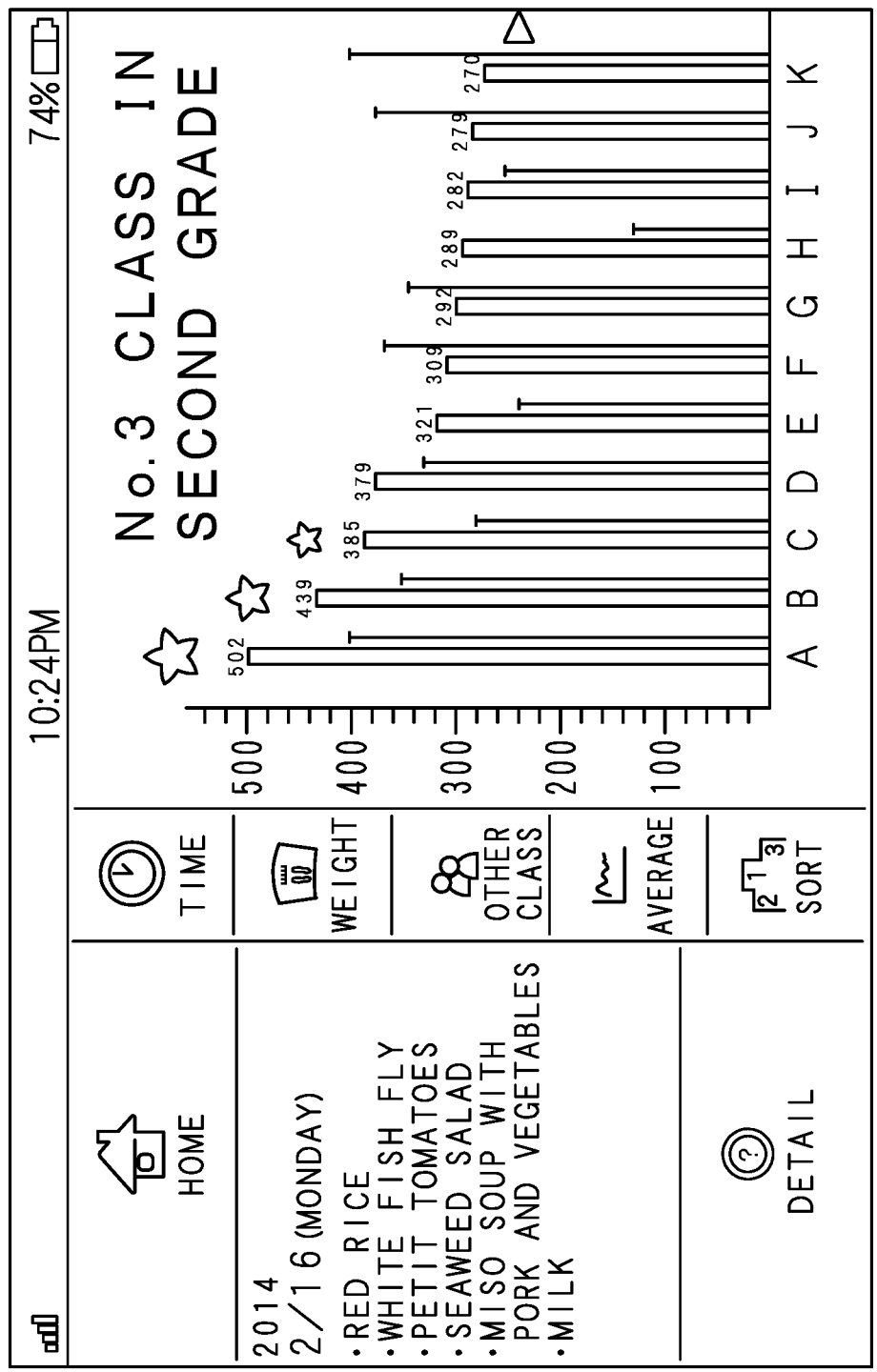
FIG. 15 is an explanatory view illustrating the fourth example of a display mode for chewing information.

FIGS. 14 and 15 are explanatory views illustrating the fourth example of display modes for chewing information. As illustrated in FIG. 14, the chewing information includes the number of chews for a student's school lunch and calories in the school lunch. As illustrated in FIG. 15, the chewing information includes the numbers of chews for students in a class and a graph showing the ranking in the class. As such, the diet of students may be recorded and visualized, which can provide new guidelines for school lunches.

Figure 16:
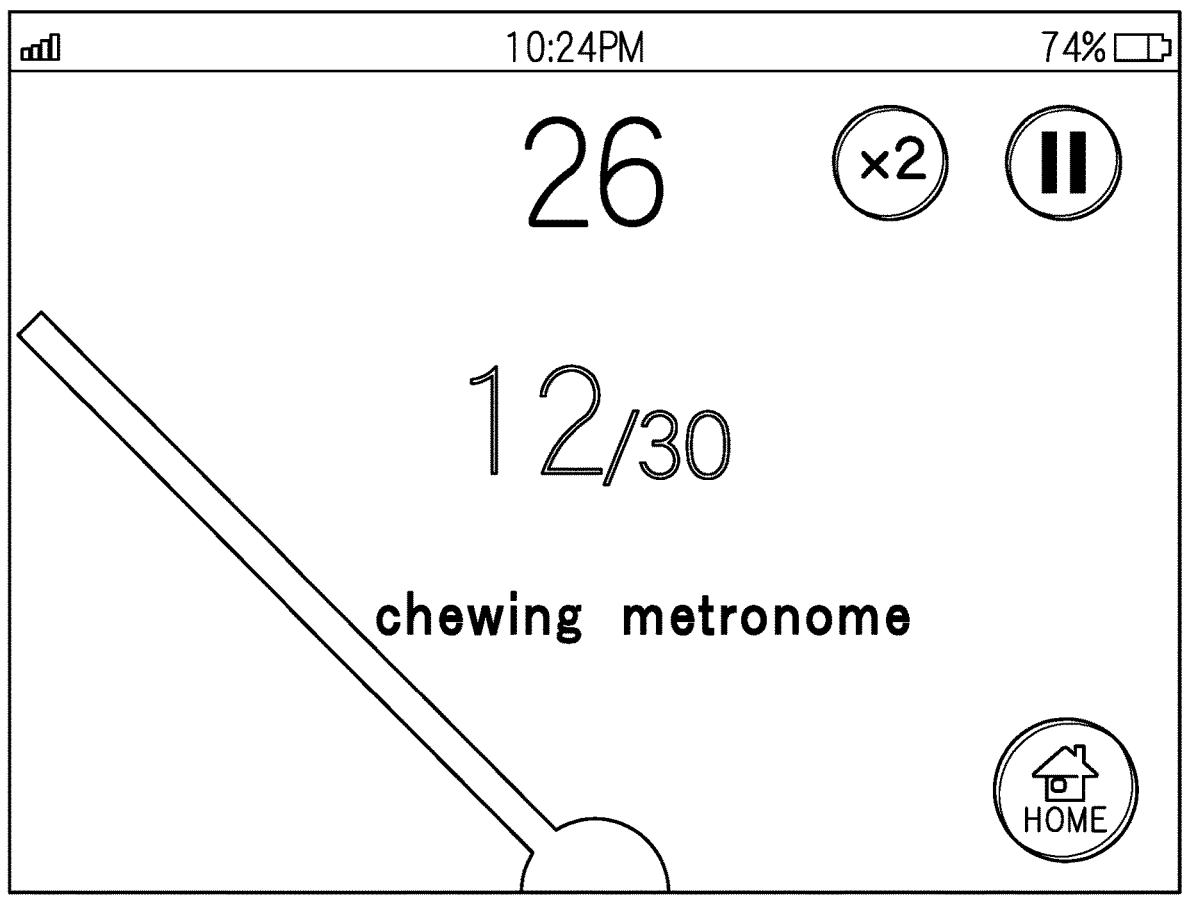
FIG. 16 is an explanatory view illustrating the fifth example of a display mode for chewing information.

FIG. 16 is an explanatory view illustrating the fifth example of a display mode for chewing information. As illustrated in FIG. 16, the chewing information includes the target speed for repetitive motion of chewing and the measured number of chews. As illustrated in FIG. 16, the target speed for repetitive motion of chewing indicates, for example, a tempo of chewing. The speed for one chew may be displayed as, for example, a metronome. In place of the display like a metronome, a display by switching between two colors, a display by blinking of one color or the like may also be employed. This allows the user to easily determine whether the measured tempo of chewing is faster or slower than the target speed, and thus may be utilized as a health management tool for a resident of a care facility or the like.

In the embodiment described above, if the user is not performing a predetermined motion such as chewing, the acceleration sensor 52 may measure the amount of activity such as a human body movement.

In the embodiment described above, an operation unit for the user to easily operate (switch, button or touch panel, for example) may be employed, and a display unit on which the operation state of the wearable measurement device 100 is displayed (LED or liquid crystal panel, for example) may also be employed.

In the embodiment described above, for setting the initial threshold C0 based on the information of a user, in place of the configuration of inputting the information of the user through external equipment, the initial threshold C0 may also be set by mounting the wearable measurement device 100 over the ear of the user who actually chews several times or speaks for calibration to assimilate the individual difference.

In the embodiment described above, while the distance sensor 40 is configured to be held in the state of not being in contact with a predetermined portion such as a jaw, the distance sensor 40 may alternatively be held in the contact state depending on a predetermined portion other than the jaw. Moreover, a sensor other than the distance sensor 40 (thermo sensor, image sensor, odor sensor, pressure sensor, microwave Doppler sensor or the like) may also be used. Furthermore, the shape or structure of the mounting part may be changed in accordance with the mounted portion, such as neck, wrist, ankle, arm, waist or the like.

(Second Embodiment)

According to the second embodiment, a band which can be wrapped around an arm is used in place of the clip 14. The distance sensor 40 may then detect the movement on the skin surface of the arm to measure a pulse as a predetermined motion.

(Third Embodiment)

In the third embodiment, a band which can be wrapped around a neck is used in place of the clip 14. The distance sensor 40 may then detect the movement on the surface of the neck to measure the sleep duration or the body condition such as breathing during sleep as a predetermined motion. Here, if the variation obtained by the distance sensor 40 is within a predetermined range, it is assumed that the user is sleeping quietly on a bed or futon, and thus the sleep duration may be measured by measuring a time period for which the detected variation is within the predetermined range. Moreover, if the variation obtained by the distance sensor 40 exceeds a predetermined threshold, it is determined that the user is breathing, and thus the breathing rate or the state of apnea may be measured by measuring the number of variations detected by the distance sensor 40 that exceeds the threshold. Furthermore, in addition to the measurement of breathing described above, the posture during sleep may be measured by the acceleration sensor 53 at the same time to more precisely and specifically measure the body condition during sleep.

(Fourth Embodiment)

In the fourth embodiment, a band which can be wrapped around a chest is used in place of the clip 14. The distance sensor 40 may then detect the movement on the surface of the chest to measure the sleep duration or the body condition such as breathing during sleep as a predetermined motion. Here, if the variation obtained by the distance sensor 40 is within a predetermined range, it is assumed that the user is sleeping quietly on a bed or futon, and thus the sleep duration may be measured by measuring a time period for which the detected variation is within the predetermined range. On the other hand, as in the third embodiment, if the variation obtained by the distance sensor 40 exceeds a predetermined threshold, it is determined that the user is breathing, and thus the breathing rate or the state of apnea may be measured by measuring the number of variations detected by the distance sensor 40 that exceeds the threshold. Furthermore, in addition to the measurement of breathing described above, the posture during sleep may be measured at the same time by the acceleration sensor 53 to more precisely and specifically measure the body condition during sleep.

The technical features described in each example embodiment of the present invention may be combined with one another, and such combinations may form new technical features.

A wearable measurement device according to the present embodiment comprises a mounting part (14) for mounting the device to a human body, a variation detection part (40) detecting a variation in distance from a predetermined portion of a human body, a posture detection part (52) detecting a posture of the variation detection part in the case where the device is mounted to the human body through the mounting part, and a measurement part (53) measuring the number of predetermined motions based on the variation detected by the variation detection part and the posture detected by the posture detection part.

A measurement method according to the present embodiment is a measurement method by a wearable measurement device including a mounting part (14) for mounting the device to a human body, and comprises the step of detecting a variation in distance from a predetermined portion of a human body by a variation detection part (40), the step of detecting a posture of the variation detection part in the case where the device is mounted to a human body through the mounting part, and the step of measuring the number of predetermined motions based on the detected variation and posture.

According to the present embodiment, the wearable measurement device may be mounted to a human body through the mounting part (14). The mounting part may have an appropriate shape depending on a mounted portion of a human body. For example, in the case of hanging over an ear, a clip having a shape adapted to the shape of the ear may be used as the mounting part. This allows the wearable measurement device to be small and less noticeable during wearing. Furthermore, the shape or structure of the mounting part may be changed in accordance with the mounted portion, such as neck, wrist, ankle, arm, waist or the like. The variation detection part (40) detects the variation in distance from the predetermined portion of a human body. The predetermined portion may be, for example, a jaw. The variation detection part may employ, for example, a distance sensor, which emits light from a light emitting unit, detects reflection light reflected at a predetermined portion by the light receiving unit, detects a distance from the predetermined portion and outputs an electric signal (voltage or current) in accordance with the detected distance at a predetermined sampling cycle. In the case where the predetermined portion is a jaw, the movement of the jaw changes the distance between the variation detection part and the jaw.

The posture detection part (52) detects the posture of the variation detection part when the device is mounted on a human body through the mounting part. The posture detection part may employ, for example, a three-axis acceleration sensor. That is, the acceleration of gravity on earth is measured by the three-axis acceleration sensor, to detect the posture (inclination) of the variation detection part. For example, the relationship between a reference posture (reference direction) of the variation detection part and the gravity direction may be determined in advance, and the individual difference at the time of mounting depending on the height, weight, age and the like of the user may be specified in accordance with the difference (difference in angles) between the gravity direction and the reference direction.

The measurement part (53) measures the number of predetermined motions based on the variation in distance detected by the variation detection part and the posture detected by the posture detection part. The measurement part measures the number of predetermined motions based on the distance detected by the variation detection part. The predetermined motion is, for example, chewing. If chewing is performed once, the peak value of the distance appears once. It is thus assumed that chewing is performed once if the peak value in the variation obtained at a predetermined sampling cycle exceeds a required threshold. By chewing the threshold based on the posture detected by the posture detection part, the individual difference of the user may be assimilated and thus the number of predetermined motions (chews) may precisely be measured.

The wearable measurement device according the present embodiment includes a decision part (54) deciding a threshold in accordance with the posture detected by the posture detection part, and the measurement part is configured to count the number of the predetermined motions if the variation detected by the variation detection part is larger than the threshold decided by the decision part.

According to the present embodiment, the decision part (54) decides a threshold in accordance with the posture detected by the posture detection part. The measurement part counts the number of predetermined motions if the variation detected by the variation detection part is larger than the threshold decided by the decision part. For example, in the case where the device is mounted to a human body through the mounting part, the threshold is made small when the distance between the variation detection part and the predetermined portion is long while the peak value in variation detected by the variation detection part is small. Moreover, in the case where the device is mounted to a human body through the mounting part, the threshold is made large when the distance between the variation detection part and the predetermined portion is short while the peak value in variation detected by the variation detection part is large. Accordingly, the individual difference of the user in the mounted state may be assimilated and thus the number of predetermined motions may precisely be measured.

As the threshold is determined by quantifying in advance the variation detected by the variation detection part in the case where a predetermined motion (e.g., chewing) is performed and the variation detected by the variation detection part in the case where a human body motion (e.g., speaking) is performed, determination can be made that a predetermined motion such as chewing is performed if the variation detected by the variation detection part is larger than the threshold and that a human body motion such as speaking is performed if the variation is not larger than the threshold. Accordingly, the predetermined motion may be distinguished from the human body motion in the measurement of the predetermined motion, which allows for precise measurement of the number of predetermined motions.

The wearable measurement device according to the present embodiment includes a human body motion detection part (52) detecting a human body motion associated with the predetermined portion. The measurement part is configured not to count the number of the predetermined motions if the human body motion detection part detects a human body motion.

According to the present embodiment, the human body motion detection part (52) detects a human body motion associated with a predetermined portion. The human body motion associated with a predetermined portion (jaw, for example) may include speaking, nodding, sneezing, swallowing, head shaking and so forth. The human body motion detection part may employ, for example, an acceleration sensor. If the human body motion is detected by the human body motion detection part, the measurement part does not count the number of predetermined motions. For example, if a human body motion is detected by the human body motion detection part in the case where chewing is measured once by the measurement part and the number of chews is increased by one, the chewing measured by the measurement part is regarded as being caused by a predetermined portion associated with the human body motion and, for example, the number of chews is not measured (correction is made to subtract one from the measured number of chews). This can prevent erroneous measurement due to human body motions such as speaking, nodding, sneezing, swallowing and head shaking, and can therefore precisely measure a predetermined motion.

The wearable measurement device according to the present embodiment includes a calculation part (55) detecting variations multiple times by the variation detection part and calculating a statistical value of the detected multiple times of variations. The measurement part is configured to count the number of the predetermined motions if the variation detected by the variation detection part is larger than the statistical value calculated by the calculation part.

According to the present embodiment, the calculation part (55) detects variations by the variation detection part multiple times, and calculates a statistical value of the detected multiple times of variations. The statistical value may be an intermediate value (median value) between the maximum value and the minimum value of the detected multiple times of variations, or a mean value of the detected multiple times of variations. The measurement part counts the number of predetermined motions if the variation detected by the variation detection part is larger than the statistical value calculated by the calculation part. This can ensure detection of the peak value of the variations obtained at a predetermined sampling cycle, and prevents erroneous measurement of the number of predetermined motions based on a variation with a small peak due to noise or the like.

It is to be noted that, as used herein and in the appended claims, the singular forms "a", "an", and "the" include plural referents unless the context clearly dictates otherwise.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A wearable measurement device, comprising:
   a clip to mount the device to a human body;
   a distance sensor detecting a variation in distance from a jaw in a case where the device is mounted to the human body through the clip;
   an acceleration sensor detecting a posture of the distance sensor in a case where the device is mounted to the human body through the clip; and
   a converter measuring a number of chews based on the variation detected by the distance sensor and the posture detected by the acceleration sensor; and
   circuitry that determines a threshold for the number of chews, wherein
   the distance sensor includes a light emitting unit and a light receiving unit,
   light emitted by the light emitting unit is reflected by the jaw and detected by the light receiving unit,
   the distance sensor detects the variation in distance according to the light detected by the light receiving unit, and
   the circuitry determines the threshold for the number of chews based upon a weighting coefficient in accordance with an angle formed by a reference direction of the distance sensor and a gravity direction.

2. The wearable measurement device according to claim 1, wherein
   the converter counts the number of chews if the variation detected by the distance sensor is larger than the threshold determined by the circuitry.

3. The wearable measurement device according to claim 1, wherein
   the acceleration sensor detects a human body motion associated with the jaw, wherein
   the converter does not count the number of chews if the acceleration sensor detects the human body motion.

4. The wearable measurement device according to claim 1, further comprising circuitry that calculates a statistical value of multiple times of variations detected by the distance sensor, wherein
   the converter counts the number of chews if the variation detected by the distance sensor is larger than the statistical value calculated by the circuitry.

5. A measurement method by a wearable measurement device including a clip to mount the device to a human body, the method comprising the steps of:
   detecting a variation in distance from a jaw by a distance sensor in a case where the device is mounted to the human body through the clip;
   detecting a posture of the distance sensor in a case where the device is mounted to the human body through the clip;
   measuring a number of chews based on the detected variation and posture;
   detecting a variation in distance by causing a light emitting unit to emit light and then detecting the light by a light receiving unit after the light has been reflected by the jaw; and
   determining a threshold for the number of chews based upon a weighting coefficient in accordance with an angle formed by a reference direction of the distance sensor and a gravity direction.

* * * * *